US00PP23995P2

(12) United States Plant Patent
Mukundan

(10) Patent No.: US PP23,995 P2
(45) Date of Patent: Oct. 15, 2013

(54) ***AGLAONEMA* PLANT NAMED 'MUKMINA'**

(50) Latin Name: *Aglaonema hybrida*
Varietal Denomination: Mukmina

(75) Inventor: Parthasarathy Mukundan, Alwarpet Chennai (IN)

(73) Assignee: K.S.G.'s Farm & Nursery, Chennai (IN)

( * ) Notice: Subject to any disclaimer, the term of this patent is extended or adjusted under 35 U.S.C. 154(b) by 108 days.

(21) Appl. No.: 13/373,835

(22) Filed: Dec. 1, 2011

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — June Hwu
(74) *Attorney, Agent, or Firm* — C. A. Whealy

(57) ABSTRACT

A new and distinct cultivar of *Aglaonema* plant named 'Mukmina', characterized by its upright and outwardly spreading plant habit; freely clumping habit; vigorous and robust growth habit; relatively short internodes giving a dense and full plant form; large oblong leaves speckled with pale yellow and yellow green-colored random markings with contrasting dark green-colored random markings and margins; dark green-colored petioles; and relative tolerance to low temperatures.

1 Drawing Sheet

Botanical designation: *Aglaonema hybrida.*
Cultivar denomination: 'MUKMINA'.

BACKGROUND OF THE INVENTION

The present invention relates to a new and distinct cultivar of *Aglaonema* plant, botanically known as *Aglaonema hybrida* and hereinafter referred to by the name 'Mukmina'.

The new *Aglaonema* plant is the product of a controlled breeding program conducted by the Inventor in Chamrajpet, Bangalore, India. The objective of the breeding program is to create new full, dense and compact *Aglaonema* plants with good plant vigor, interesting and unique leaf shapes and variegation patterns, resistance to pathogens and pests and tolerance to low temperatures.

The new *Aglaonema* plant is the product of a cross-pollination conducted by the Inventor on Mar. 6, 2004 of *Aglaonema hybrida* 'Gold Dust', disclosed in U.S. Plant Pat. No. 17,497, as the female, or seed, parent with a selection of *Aglaonema costatum* N.E. Br. var. *costatum f. costatum* commonly referred to as Spotted Evergreen, not patented, as the male, or pollen, parent. The new *Aglaonema* plant was discovered and selected by the Inventor in September, 2005 as a single plant from within the resultant progeny of the stated cross-pollination in a controlled environment in Tiruporur, Chennai, India.

Asexual reproduction of the new *Aglaonema* plant by cuttings and divisions in a controlled environment in Tiruporur, Chennai, India since September, 2005 has shown that the unique features of this new *Aglaonema* plant are stable and reproduced true to type in successive generations of asexual reproduction.

SUMMARY OF THE INVENTION

Plants of the new *Aglaonema* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mukmina'. These characteristics in combination distinguish 'Mukmina' as a new and distinct *Aglaonema* plant:

1. Upright and outwardly spreading plant habit.
2. Freely clumping habit.
3. Vigorous and robust growth habit.
4. Relatively short internodes giving a dense and full plant form.
5. Large oblong leaves speckled with pale yellow and yellow green-colored random markings with contrasting dark green-colored random markings and margins.
6. Dark green-colored petioles.
7. Relatively tolerant to low temperatures.

Plants of the new *Aglaonema* differ from plants of the female parent, 'Gold Dust', in the following characteristics:

1. Plants of the new *Aglaonema* are taller and more vigorous than plants of 'Gold Dust'.
2. Leaves of plants of the new *Aglaonema* are larger than and not as flat as leaves of plants of 'Gold Dust'.
3. Plants of the new *Aglaonema* and 'Gold Dust' differ in leaf coloration, variegation pattern and midvein color.
4. Plants of the new *Aglaonema* and 'Gold Dust' differ in leaf petiole color.

Plants of the new *Aglaonema* differ from plants of the male parent selection in the following characteristics:

1. Plants of the new *Aglaonema* are more vigorous and more uniform than plants of the male parent selection.
2. Plants of the new *Aglaonema* have larger leaves than plants of the male parent selection.
3. Plants of the new *Aglaonema* and the male parent selection differ in leaf shape, coloration, variegation pattern and midvein color.

Plants of the new *Aglaonema* can be compared to plants of *Aglaonema hybrida* 'Emerald Star', disclosed in U.S. Plant Pat. No. 10,659. In side-by-side comparisons conducted in Chamrajpet, Bangalore, India, plants of the new *Aglaonema* differed from plants of 'Emerald Star' in the following characteristics:

1. Plants of the new *Aglaonema* had shorter internodes and were denser and fuller than plants of 'Emerald Star'.
2. Plants of the new *Aglaonema* and 'Emerald Star' differed in leaf shape, coloration and variegation pattern.
3. Plants of the new *Aglaonema* and 'Emerald Star' differed in leaf petiole color.

Plants of the new *Aglaonema* can also be compared to plants of *Aglaonema hybrida* 'Stars', disclosed in U.S. Plant Pat. No. 10,247. In side-by-side comparisons conducted in Chamrajpet, Bangalore, India, plants of the new *Aglaonema* differed from plants of 'Stars' in the following characteristics:

1. Plants of the new *Aglaonema* had shorter internodes and were denser and fuller than plants of 'Stars'.
2. Plants of the new *Aglaonema* and 'Stars' differed in leaf shape, coloration and variegation pattern.
3. Plants of the new *Aglaonema* and 'Stars' differed in leaf petiole color.

BRIEF DESCRIPTION OF THE PHOTOGRAPH

The accompanying photograph illustrates the overall appearance of the new *Aglaonema* plant showing the colors as true as it is reasonably possible to obtain in colored reproductions of this type. Colors in the photograph may differ slightly from the color values cited in the detailed botanical description which accurately describe the colors of the new *Aglaonema* plant. The photograph comprises a side perspective view of a typical plant of 'Mukmina' grown in a container.

DETAILED BOTANICAL DESCRIPTION

The aforementioned photographs and following observations and measurements describe plants grown in 25-cm containers in Miami, Fla. during the summer and autumn in a polypropylene-covered shadehouse. Plants were grown under environmental conditions and cultural practices which approximate those generally used in commercial *Aglaonema* production. During the production of the plants, day temperatures ranged from 27° C. to 37° C., night temperatures ranged from 15° C. to 26° C. and light levels averaged 1,500 foot-candles. Plants were one year old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'Mukmina'.

Parentage:

*Female, or seed, parent.*—*Aglaonema hybrida* 'Gold Dust', disclosed in U.S. Plant Pat. No. 17,497.

*Male, or pollen, parent.*—Selection of *Aglaonema costatum* N.E. Br. var. *costatum f. costatum* commonly referred to as Spotted Evergreen, not patented.

Propagation:

*Type.*—By cuttings and divisions.

*Time to initiate roots, summer.*—About 21 to 28 days at 25° C. to 32° C.

*Time to initiate roots, winter.*—About 30 to 40 days at 12° C. to 25° C.

*Time to produce a rooted young plant, summer.*—About 30 to 35 days at 25° C. to 32° C.

*Time to produce a rooted young plant roots, winter.*—About 45 to 60 days at 12° C. to 25° C.

*Root description.*—Fleshy, medium in thickness; off-white in color.

*Rooting habit.*—Freely branching; profuse, high density.

Plant description:

*Plant and growth habit.*—Upright and outwardly spreading plant habit; freely clumping habit; relatively short internodes giving a compact, dense, full and symmetrical habit; vigorous growth habit; developing leaves initially upright, then spreading outwardly with development.

*Plant height, from soil level to top of leaf plane.*—About 56 cm.

*Plant diameter or spread.*—About 95 cm.

*Stem description.*—Clumping habit: Plants of the new *Aglaonema* are freely clumping with about 22 clumps developing per plant. Aspect: Mostly upright. Strength: Strong; somewhat flexible. Diameter, at the base: About 1.9 cm. Internode length, at the base: About 1 cm. Color: Close to 144A. Cataphylls: None observed.

Foliage description:

*Arrangement.*—Alternate to whorled; simple.

*Length.*—About 25 cm.

*Width.*—About 14 cm.

*Shape.*—Oblong.

*Apex.*—Cuspidate.

*Base.*—Obtuse with oblique tendencies.

*Margin.*—Entire; slightly undulate, curled.

*Texture, upper and lower surfaces.*—Smooth, glabrous.

*Venation pattern.*—Pinnate.

*Color.*—Developing leaves, upper surface: Along midveins, margins and random markings, close to 147A; contrasted with random markings, closest to 4D; midvein, close to 148D; lateral venation, same as leaf coloration. Developing leaves, lower surface: Along midveins, margins and random markings, closest to 137A; contrasted with random markings, closest to 157A to 157C; midvein, close to 146A to 146B; lateral venation, same as leaf coloration. Fully expanded leaves, upper surface: Along midveins, margins and random markings, close to 147A; contrasted with random markings, closest to 4D, 150B, 150C, 150D and/or 154D; midvein, close to 148C to 148D; lateral venation, same as leaf coloration. Fully expanded leaves, lower surface: Along midveins, margins and random markings, closest to 137A; contrasted with random markings, closest to 157A to 157C; midvein, close to 146A to 146B; lateral venation, same as leaf coloration.

*Petiole.*—Aspect: Mostly erect, outwardly spreading with development. Length: About 19.5 cm. Diameter, distal: About 5 mm. Diameter, proximal, flattened: About 2.2 cm. Strength: Strong; flexible. Color, distal: Close to 147A. Color, proximal: Between 147B and 146A; area adjacent to stem, close to 157A to 157C. Wing length: About 10 cm. Wing diameter, base: About 5 mm. Wing color, inner and outer surfaces: Close to 147A; towards the base, between 147B and 146A; area adjacent to stem, close to 157A to 157C.

Inflorescence description: Inflorescence development has not been observed on plants of the new *Aglaonema*.

Disease & pest resistance: Plants of the new *Aglaonema* have not been observed to be resistant to pathogens or pests common to *Aglaonema*.

Temperature tolerance: Plants of the new *Aglaonema* have been observed to be relatively low temperature tolerant and to tolerate temperatures ranging from about 15° C. to about 40° C.

It is claimed:

1. A new and distinct *Aglaonema* plant named 'Mukmina' as illustrated and described.

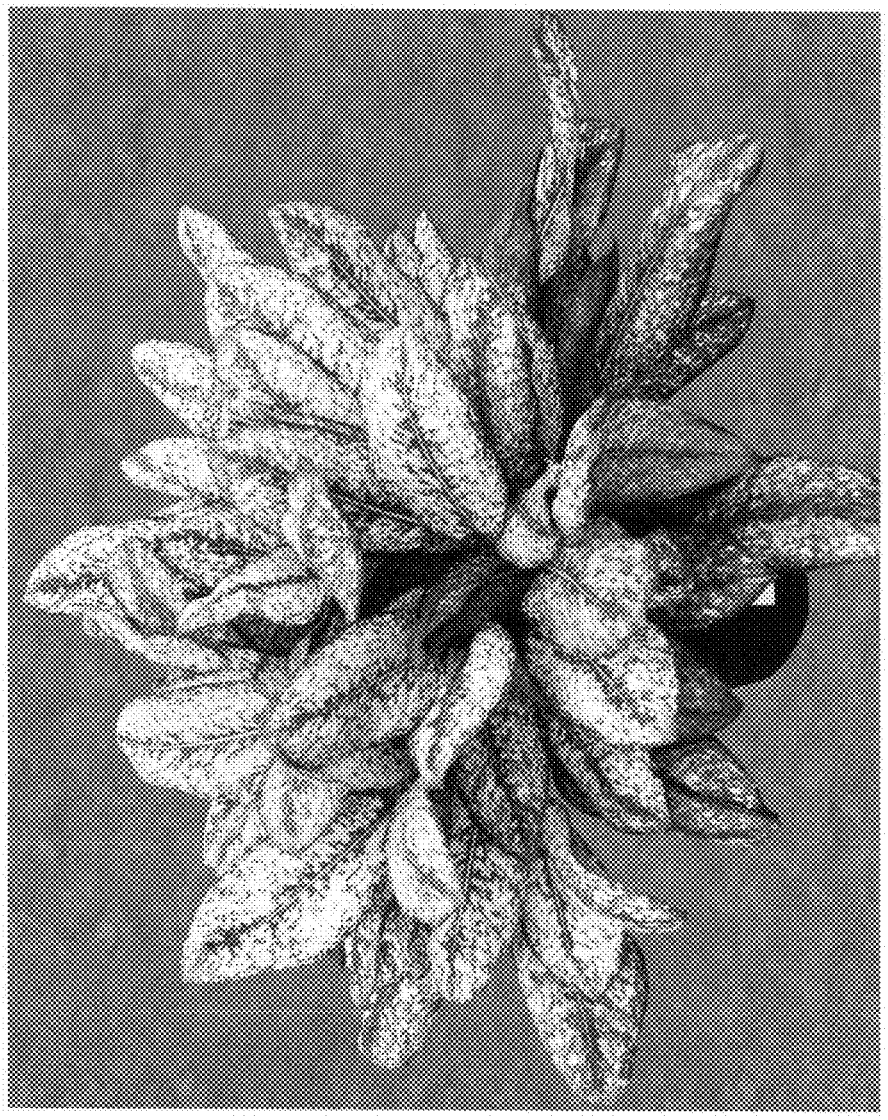

* * * * *